United States Patent [19]

Kurtz et al.

[11] Patent Number: 4,634,703
[45] Date of Patent: Jan. 6, 1987

[54] METHOD FOR ALLEVIATION OF PANIC DISORDERS

[75] Inventors: Neil M. Kurtz, Westport, Conn.; Roger E. Newton, Evansville, Ind.; Davis L. Temple, Jr., Wallingford, Conn.

[73] Assignee: Bristol-Myers Company, New York, N.Y.

[21] Appl. No.: 791,182

[22] Filed: Oct. 25, 1985

[51] Int. Cl.⁴ .................. A61K 31/50; A61K 31/495
[52] U.S. Cl. .................................................. 514/252
[58] Field of Search ........................................ 514/252

[56]  References Cited

U.S. PATENT DOCUMENTS

| 3,717,634 | 2/1973 | Wu et al. | 260/308 R |
| 3,976,776 | 8/1976 | Wu et al. | 514/252 |
| 3,987,052 | 10/1976 | Hester, Jr. | 260/308 R |
| 4,182,763 | 1/1980 | Casten et al. | 514/252 |
| 4,508,726 | 4/1985 | Coleman | 514/220 |

OTHER PUBLICATIONS

Y. H. Wu, et al., J. Med. Chem., 15, 477 (1972).
L. E. Allen, et al., Arzneim. Forsch., 24, No. 6, 917–922 (1974).
G. L. Sathananthan, et al., Current Therapeutic Research, 18/5 701–705 (1975).
Breier, et al., Am. J. Psychiatry, 142:7, pp. 787–797 (1985).
Sheehan, New England Journal of Medicine, 307, pp. 156–158 (1982).
Shader, et al., J. Clin. Psychopharmacology, 2/6 Supplement, pp. 2S–26S (1982).
Matuzas, et al., Arch. Gen. Psychiatry, 40, pp. 220–222 (1983).

*Primary Examiner*—Stanley J. Friedman
*Attorney, Agent, or Firm*—Richard P. Ryan; Robert E. Carnahan; Robert H. Uloth

[57]  ABSTRACT

Buspirone and its pharmaceutically acceptable salts are useful in alleviation of panic disorders which can take the form of clinical syndromes comprising, for example, panic attacks, agoraphobia and phobic anxiety.

8 Claims, 1 Drawing Figure

METHOD FOR ALLEVIATION OF PANIC DISORDERS

FIELD OF THE INVENTION

This invention is concerned with a drug bioaffecting body-treating process which employs the pyrimidine compound 8-[4-[4-(2-pyrimidinyl)-1-piperazinyl]butyl]-8-azaspiro[4.5]decane-7,9-dione or a pharmaceutically acceptable acid addition salt thereof.

BACKGROUND OF THE INVENTION

The pyrimidine compound with which the present invention is concerned has the following structural formula

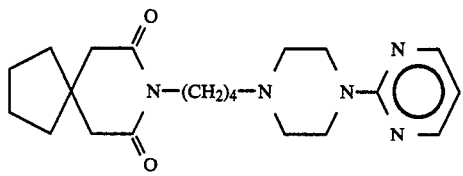

and is known as buspirone. The hydrochloride salt has been referred to in the prior art as MJ 9022-1 and as buspirone hydrochloride. Other acid addition salts thereof are named by combining "buspirone" with the appropriate word to define the acid from which it is prepared as in "buspirone hydrochloride". The latter is the United States Adopted Name (USAN); refer to *J. American Med. Assoc.* 225, 520 (1973).

The synthesis of the compound and the disclosure of its psychotropic properties are described in the following patents and publications.

1. Y. H. Wu, et al., *J. Med. Chem.*, 15, 477 (1972).
2. Y. H. Wu, et al., U.S. Pat. No. 3,717,634 which issued Feb. 20, 1973.
3. L. E. Allen, et al., *Arzneium. Forsch.*, 24, No. 6, 917-922 (1974).
4. G. L. Sathananthan, et al., *Current Therapeutic Research*, 18/5, 701-705 (1975).
5. Y. H. Wu, et al., U.S. Pat. No. 3,976,776, issued Aug. 24, 1976.

The use of buspirone hydrochloride as a novel antianxiety agent for the treatment of neurotic patients is described in G. P. Casten, et al., U.S. Pat. No. 4,182,763, issued Jan. 9, 1980. Currently, a New Drug Application (NDA) is pending before the U.S. Food & Drug Administration for the use of buspirone in treatment of anxiety neurosis. In addition, other clinical studies are being conducted to lend support to the use of buspirone for the therapeutic method of the instant invention.

The present invention can be distinguished from the above prior art in that it is directed to a distinct patient population characterized by a disease state different from that related to the anxiolytic process disclosed in the prior art. Support for this distinction is found in the reference, "The Diagnostic Validity of Anxiety Disorders and Their Relationship to Depressive Illness", by A. Breier, et al., in *Am. J. Psychiatry*, 142:7 (July, 1985), pages 787-796. The diagnosis and treatment of panic disorders has been recently reviewed; cf: D. V. Sheehan, "Panic Attacks and Phobias", *New England Journal of Medicine*, 307, pages 156-158, 1982; R. I. Shader, et al., "Panic Disorders: Current Perspectives", *J. Clin. Pyschopharmacology*, 2/6 Supplement, pages 2S-26S, 1982; and W. Matuzas, et al., "Treatment of Agoraphobia and Panic Attacks", *Arch. Gen. Psychiatry*, 40, pages 220-222, 1983.

Although panic disorder is a relatively new diagnosis, the basic diagnostic concepts are well known to those skilled in the art and are clearly differentiated from generalized, persistent anxiety. Although the prior art references concerning buspirone disclose the compounds described in the instant application and their tranquilizing and anti-anxiety effects, none of these prior art buspirone references disclose or suggest that these compounds are useful to treat or prevent panic disorders which is the applicants' claimed invention.

An example for comparison which distinguishes use in generalized anxiety from use in panic disorder is the drug alprazolam which was disclosed in U.S. Pat. No. 3,987,052, issued October, 1976 to Hester as having sedative, tranquilizing and muscle relaxant effects and could be used to alleviate tension and anxiety in mammals. U.S. Pat. No. 4,508,726, issued April, 1985, to Coleman discloses and claims the treatment of panic disorders with alprazolam. Further, U.S. Pat. No. 4,508,726 admits that alprazolam had been previously disclosed for the management of anxiety disorders. Alprazolam, a benzodiazepine compound, bears no structural or biochemical relationship to buspirone and would not suggest its usefulness in panic disorders.

In summary, buspirone and its pharmaceutically acceptable salts bear no structural resemblance to any therapeutic agent alleged to be useful in the treatment of panic disorders. It is now appreciated by those skilled in the art that generalized anxiety and panic disorders are distinguishable disease states with differently defined patient populations. There also exists nothing in the prior art which teaches or suggests that the instant compounds would be useful in alleviation of panic disorder.

SUMMARY OF THE INVENTION

The process of the present invention is intended for the alleviation of panic disorders of which panic attacks, agoraphobia, and phobic anxiety are specific examples. The process essentially involves administration of buspirone, or a pharmaceutically acceptable acid addition salt thereof, to one in need of such treatment. For use in the instant process oral administration of buspirone hydrochloride from about 10 to 60 mg per day in divided doses is anticipated as being the preferred dosage regimen.

DETAILED DESCRIPTION OF THE INVENTION

Figure 1:
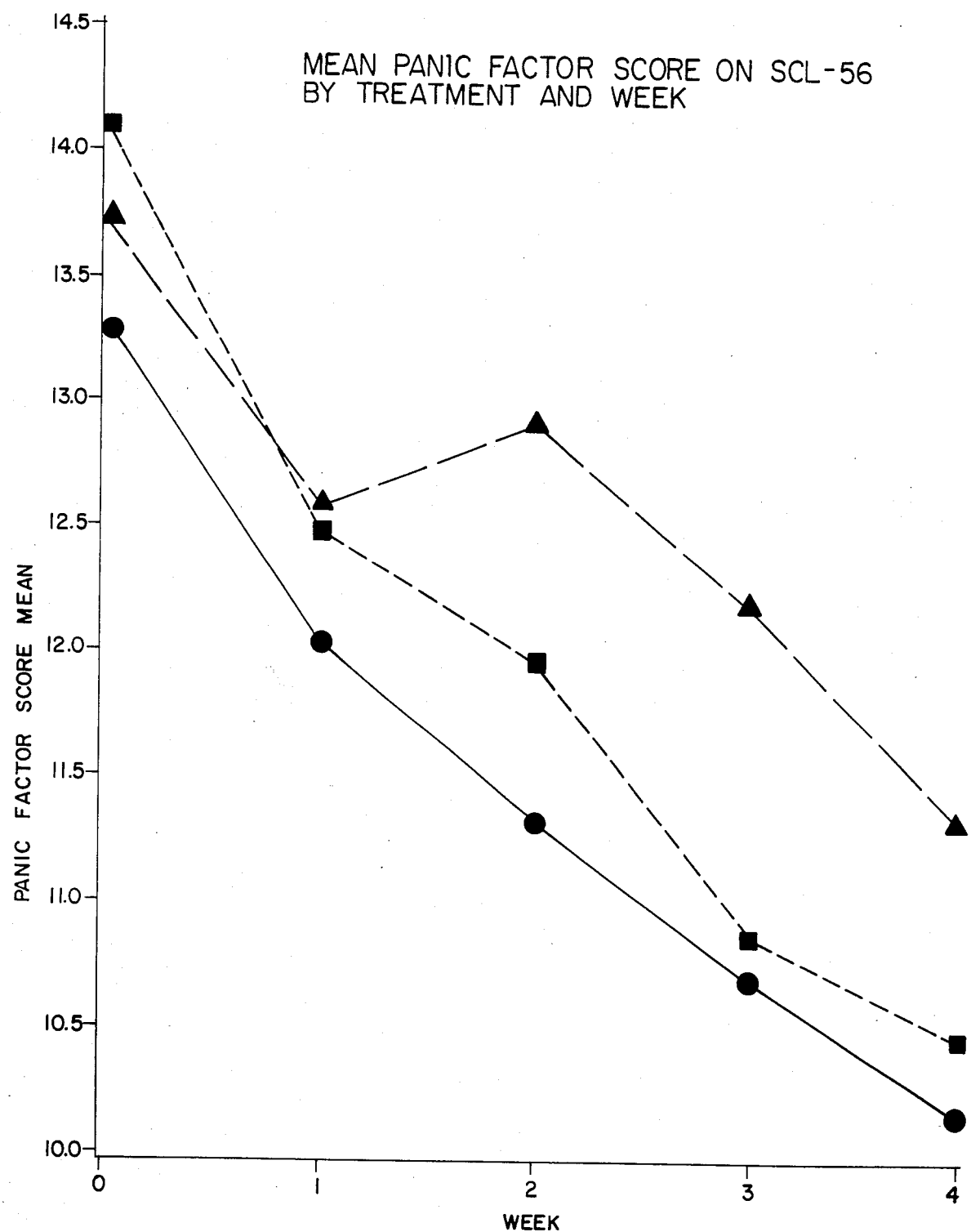
FIG. 1 graphically demonstrates the time versus treatment relationship over a four-week treatment period of mean patient scores of the panic factor for each of the three treatment groups.

Panic disorders are best defined clinically by the frequent occurrence of panic attacks in patients. A panic attack is described as a sudden surge of intense discomfort and/or fear which can occur either spontaneously seemingly without cause or can occur as situational episodes. Within 10 minutes of the onset of the panic attack a variety of characteristic symptoms may develop. These symptoms can include shortness of breath, choking or smothering sensations, palpitations or accelerated heart rate, chest pain, sweating, faintness, dizziness, lightheadedness, nausea or abdominal distress, depersonalization or derealization, numbness or tingling sensations, hot flashes or chills, trembling or shaking, a fear of dying, or a fear of becoming insane or losing mental control. The frequency and severity of these attacks can result in phobic anxiety and behavior which can, in certain instances, cause the patient to be housebound or severely restricted in social behavior.

To date, various treatments have been employed for treatment of patients suffering from panic disorders. These treatments include hypnosis and behavior therapies as well as pharmacotherapy. Imipramine hydrochloride and phenelzine sulfate are the most widely prescribed drugs for this indication and, although effective for relief of panic attacks, have undesirable side effects which limit their usefulness. Clinical results with benzodiazepines appear to be variable.

It has now been found that buspirone alleviates some of the symptoms associated with panic disorders. This finding was made by analysis of changes in panic disorder related items contained in standard psychometric instruments. To illustrate, a group of patients suffering from anxiety but with significant symptoms of panic disorder were assessed over a 4-week treatment period using a panic disorder factor which was extracted from the Hopkins Symptom Checklist (SCL-56). The Hopkins Symptom Checklist (cf: L. R. Derogatis, et al., *Behavioral Science*, 19:1 (January, 1974) pages 1-15) is a self-report symptom inventory representing repeated factors comprising five symptom dimensions including panic attack items. Buspirone and diazepam produced significantly greater improvement in relieving symptoms of panic disorder than did placebo; see FIG. 1.

FIG. 1 shows the time versus treatment relationship of the mean patient panic factor score by drug treatment group. The panic factor score is obtained for each patient at weeks 0 through 4 by summing the numerical values assigned to each panic factor symptom item according to severity and/or frequency being experienced. The higher the patient score, the greater the degree of illness. As can be seen, there is little difference in mean score between the three treatment groups for weeks 0 and 1. From week 2 through 4 the buspirone and diazepam treatment groups show a trend to greater improvement than the placebo treatment group.

Buspirone, a drug which is structurally unrelated to any presently used agent in treatment of panic disorders, is currently under study in prospective clinical trials in order to gain approval from the U.S. Food & Drug Administration for the use of buspirone for this indication.

The process of the present invention essentially involves administration of buspirone, or a pharmaceutically acceptable acid addition salt thereof, to a patient in need of such treatment. Pharmaceutically acceptable acid addition salts of buspirone and methods of pharmaceutical formulation are described in the above patents of Wu, et al., U.S. Pat. No. 3,717,634 and Casten, et al., U.S. Pat. No. 4,182,763 which are incorporated herein in their entirety by reference.

Administration of buspirone according to the present invention may be made by the parenteral, oral, or rectal routes. The oral route is preferred, however, The clinical dosage range for alleviation of panic disorders is expected to be about the same to slightly higher compared with that for anti-anxiety usage, but can vary to some extent. In general, the expected amount of buspirone administered would be less than about 100 mg per day, generally in the 20 mg to 80 mg range, and preferably in the range of 30–60 mg per day. Since the dosage should be tailored to the individual patient, the usual practice is to commence with a dose of about 5 mg administered two or three times per day and then to increase the dose every two or three days by 5 mg at each dosage time until the desired response is observed or until the patient exhibits side effects. Single daily dosage may be applicable in some instances.

What is claimed is:

1. A method for alleviation of panic disorders which comprises administering a non-toxic therapeutically effective dose of buspirone or a pharmaceutically acceptable acid addition salt thereof to a patient in need of such treatment.

2. The method of claim 1 wherein buspirone hydrochloride is employed and dosage is by the oral route.

3. The method of claim 1 wherein panic attacks is the specific panic disorder afflicting said patient.

4. The method of claim 1 wherein agoraphobia is the specific panic disorder afflicting said patient.

5. The method of claim 1 wherein phobic anxiety is the specific panic disorder afflicting said patient.

6. The method of claim 2, 3, 4, or, 5 wherein said mammal is an adult and a daily dose of from about 10 mg to 60 mg is employed.

7. The method of claim 6 wherein said daily dose is divided and administered b.i.d.

8. The method of claim 6 wherein said daily dose is divided and administered t.i.d.

* * * * *